(12) United States Patent
Pachl et al.

(10) Patent No.: US 6,399,293 B1
(45) Date of Patent: Jun. 4, 2002

(54) METHODS AND TEST DEVICES FOR DETERMINATION OF GLYCATED HAEMOGLOBIN

(75) Inventors: Rudolf Pachl, Ellerstadt; Carina Horn, Hähnlein, both of (DE)

(73) Assignee: Roche Diagnostics GmbH, Manheim (DE)

( * ) Notice: Subject to any disclaimer, the term of this patent is extended or adjusted under 35 U.S.C. 154(b) by 0 days.

(21) Appl. No.: 09/395,228

(22) Filed: Sep. 13, 1999

(30) Foreign Application Priority Data

Sep. 21, 1998 (DE) ........................................ 198 43 0494

(51) Int. Cl.⁷ ................................................ C12Q 1/00
(52) U.S. Cl. ............................. 435/4; 422/60; 435/25; 435/970
(58) Field of Search .................... 435/4, 7.92, 7.95, 435/25, 970; 422/56–58, 60; 436/66, 67, 169, 177, 539, 828

(56) References Cited

U.S. PATENT DOCUMENTS

| 4,861,728 A | | 8/1989 | Wagner ...................... 436/501 |
| 5,397,711 A | * | 3/1995 | Finckh ........................ 436/164 |
| 5,426,030 A | | 6/1995 | Rittersdorf et al. ........... 435/11 |
| 5,506,144 A | * | 4/1996 | Sundrehagen ................. 436/66 |
| 5,631,364 A | | 5/1997 | Sundrehagen et al. ...... 540/128 |
| 5,766,552 A | * | 6/1998 | Doshi et al. ................. 422/101 |
| 5,882,935 A | * | 3/1999 | Hirai et al. .................... 436/67 |
| 5,972,294 A | * | 10/1999 | Smith et al. .................. 422/58 |
| 6,054,039 A | * | 4/2000 | Shieh ........................... 205/792 |
| 6,174,734 B1 | * | 1/2001 | Ito et al. ...................... 436/518 |

FOREIGN PATENT DOCUMENTS

| DE | 3720736 A1 | 1/1989 | ............. C07F/5/02 |
| EP | 0 471 774 B1 | 1/1995 | .......... G01N/33/72 |
| EP | 0 557 357 B1 | 3/1995 | ............. C07F/5/02 |
| WO | WO 90/13818 | 11/1990 | .......... G01N/33/72 |
| WO | WO 92/08722 | 5/1992 | ............. C07F/5/02 |
| WO | WO 96/03657 | 2/1996 | .......... G01N/33/68 |

OTHER PUBLICATIONS

Rudolf Fluckiger, et al., "Quantitation of Glycosylated Hemoglobin by Boronate Affinity Chromatography," Diabetes 33:73–76 (1984).

Richard D. Forrest, et al., "Four Assay Methods for Glycated Hemoglobin Compared as Screening Tests for Diabetes Mellitus: The Islington Diabetes Survey," Clinical Chemistry 34:145–148 (1988).

J. Karl, et al., "Development and Standardization of a New Immunoturbidimetric HbA1c Assay," Klin. Lab. 39:991–996 (1993).

Lionel Menard, et al., "Quantitative Determination of Glycosylated Hemoglobin A1 by Agar Gel Electophoresis," Clinical Chemistry 26:1598–1602 (1980).

Von Cornelia Maria Niederau, et al., "Analyseverfahren fur glykosidierte Hamoglobine Ein Methodenvergleich," J. Clin. Chem. Clin. Biochem. 19:1097–1101 (1981).

C. M. Niederau, et al., "Hamoglobin A1 Analyse mit dem Mikrosauleverfahren und Ergebnisse der Ringversuche," Lab. Med. 8:74–78 (1984).

Gerhard Oremek, et al., "Determination of glycated hemoglobin by affinity chromatography," Clinica Chemica Acta. 168:81–86 (1987).

G. Schmid, et al., "Determination of Glycosylated Hemoglobin by Affinity Chromatography," Fresenius Z Anal. Chem. 317:703–704 (1984).

A. G. Schnek, et al., "The Relation between the Minor Components of Whole Normal Human Adult Hemoglobin as Isolated by Chromatography and Starch Block Electrophoresis," J. Am. Chem. Soc., 83:1472–1478 (1961).

D. G. Willey, et al., "Glycosylated haemoglobin and plasma glycoprotein assays by affinity chromatography," Diabetologia 27:56–58 (1984).

* cited by examiner

Primary Examiner—Ralph Gitomer
(74) Attorney, Agent, or Firm—Woodard, Enhardt, Naughton, Moriarity & McNett

(57) ABSTRACT

This invention relates to a test element and a method for determining the ratio of glycated to non-glycated haemoglobin in a sample, for example, in a blood sample that is provided as a fresh sample, a dried sample or a haemolysed sample. The test element can include different zones for receiving the sample, serving as a depot for reagents such as non-immobilized signal-generating molecules or haemolysis reagents, separating reagents from the sample, and detecting heamoglobin. The zones are provided on a porous matrix and in fluid contact with each other. The method uses the test element and determines the ratio of glycated to non-glycated haemoglobin in a sample, by contacting the sample with an excess of signal generating molecules to bind to the glycated haemoglobin. The non-bound signal generating molecules are separated from the sample, and the amount or concentration of haemoglobin and/or glycated haemoglobin bound signal generating molecules are determined. The signal generating molecules can be selected to be a direct label, an enzyme label or a radiolabel, which can be attached to the glycated haemoglobin via a boronic acid group or another specific binding partner or antibody.

15 Claims, 2 Drawing Sheets

METHODS AND TEST DEVICES FOR DETERMINATION OF GLYCATED HAEMOGLOBIN

BACKGROUND OF THE INVENTION

The invention concerns a method for the determination of the ratio of glycated to non-glycated haemoglobin in a sample. The invention also concerns an analytical test element which is suitable for determining the ratio of glycated to non-glycated haemoglobin in a sample on the basis of the new method according to the invention.

The glycation of haemoglobin and serum proteins is increased in patients with diabetes mellitus. The increase depends on the glucose concentration and the period of incubation of the protein with glucose. In these cases the glycation of serum proteins, including haemoglobin, does not take place enzymatically but rather uncatalysed by chemical reaction of glucose with amino groups of the proteins. Experts assume that the concentration of a certain protein-glucose adduct reflects the glucose concentration over a particular period as well as the turn-over rate of the protein. Glycated haemoglobin is regarded as an indicator of the mean blood glucose concentration during the last two to three months before blood withdrawal and examination. Glycated serum protein reflects blood glucose concentration during a shorter time span. Hence the determination of glycated protein such as glycated haemoglobin (in particular HbA1c) or glycated serum protein is very important for the long-term glycaemic control of diabetes patients. In this connection the ratio of glycated haemoglobin to total haemoglobin in a blood sample is of particular relevance.

The content and determination of haemoglobin A1 (HbA1c) and of the medically equivalent glycated haemoglobin is an important medical criterion for the long-term metabolic control of diabetic patients. In ca. 80% of the glycated haemoglobin the glucose is located on the N-terminal valine of the $\beta$ chain (so-called "HbA1c") whereas the carbohydrate residues of the remaining glycated haemoglobin are located at other sites or other sugars apart from glucose have reacted with haemoglobin.

At least 5 methodologies are at present commonly used to determine glycated haemoglobin in blood. A brief description is given in the following:

1. Ion Exchange Chromatography With a Microcolumn

The ion exchange chromatography with the aid of a micro-column is described for example in J.Clin.Chem.Clin. Biochem., 19, 1097–1101 (1981), Lab.Med., 8, 74–78 (1984) and J.Am.Chem.Soc., 83, 1472–1478 (1961). In this method the haemoglobin of a haemolysed sample is bound to an ion exchanger and fractionally eluted. The labile aldimine form of HbA1 is degraded by an eliminator in the haemolysis reagent. Non-glycated haemoglobin (HbA0) and glycated haemoglobin (HbA1) are separated on the basis of the different charge of the two types of haemoglobin. The amounts of glycated and non-glycated haemoglobin are measured with a photometer at a wavelength of 415 nm. EDTA blood and heparin blood can be used in this method as a sample.

A disadvantage in determining glycated haemoglobin by ion exchange chromatography with a microcolumn is the high temperature and pH dependency and interference by labile precursors of glycated haemoglobin, non-glucose adducts of haemoglobin and other haemoglobin variants. Moreover this method can only be carried out in an analytical laboratory by trained staff.

2. Electrophoretic Method

The electrophoretic method for determining glycated haemoglobin is described for example in Clin.Chem., 34, 145–148 (1988) and Clin.Chem., 26, 1598–1602 (1980). The method separates HbA1 and HbA0 by the action of endoosmosis due to the different charges on glycated and non-glycated haemoglobins. The electrophoresis film is evaluated with a densitometer. EDTA blood and oxalate blood can be used as sample materials. Heparinized fresh blood cannot be used for this method.

Like the ion exchange chromatography with a microcolumn, labile precursors of glycated haemoglobin, non-glucose adducts and other haemoglobin variants interfere with the electrophoretic method. The electrophoretic method can also only be carried out in an analytical laboratory by trained staff.

3. Affinity Chromatography

The determination of glycated haemoglobin by means of affinity chromatography is based on the principle of separating glycated and non-glycated haemoglobin on an agarose column which contains covalently bound aminophenylboronic acid. The method is described for example in Diabetes, 33, 73–76 (1984), Fresenius Z.Anal.Chem., 317, 703–704 (1984), Diabetologia, 27, 56–58 (1984) and in Clin.Chim.Acta. 168, 81–86 (1987).

The trihydroxyaminophenylborane immobilized on the agarose column forms a complex with the ketoamine form of glycated haemoglobin so that this fraction is retained on the column. The non-glycated haemoglobin passes through the column without delay as a main fraction and is collected. The glycated haemoglobin is eluted from the column with buffer containing sorbitol and is also collected separately. The amount of glycated haemoglobin is calculated from the absorbances of the fractions.

The separation by affinity chromatography of glycated and non-glycated haemoglobin is characterized in that there is hardly any influence by pH and temperature and there are no interferences by the labile aldimine form, other haemoglobin variants or non-glucose adducts of haemoglobin. Haemolysates of fluoride and EDTA blood are suitable as sample material. The method comprises several process steps and can only be carried out in an analytical laboratory by trained staff.

4. Immunological Determination

The immunological determination of glycated haemoglobin is described for example in Klin.Lab., 39, 991–996 (1993). In this method the glycated haemoglobin (HbA1c) of the sample reacts with anti-HbA1c antibodies in a first reaction step. Since the HbA1c-specific epitope only occurs once in each $\beta$ chain of the glycated haemoglobin, there is no aggregation of the antigen-antibody complex. Only after addition of a polyhapten which has several HbA1c-specific epitopes, do the molecules react with the excess antibodies from the first reaction and an insoluble immune complex is formed. This can be measured turbidimetrically. The turbidimetric signal is inversely proportional to the concentration of glycated haemoglobin in the sample.

A disadvantage of this method which comprises several processing steps, is that it can only be carried out in a specialized analytical laboratory.

5. Detection of Glycated Haemoglobin with the Aid of Boronic Acid-dye Conjugates The detection of glycated haemoglobin with the aid of boronic acid-dye conjugates is described for example in EP-B 0 471 774, EP-B 0 557 357 and in U.S. Pat. No. 5,506,144 and U.S. Pat. No. 5,631,364. In this method a conjugate composed of phenylboronic acid and a blue dye, bind to the glycated sites of glycated haemoglobin after lysis of the erythrocytes. For this a reagent mixture containing the boronic acid-dye conjugate is added to the haemolysate after haemolysing the blood sample, the total amount of haemoglobin is precipitated and separated from the remainder of the sample by filtration. The boronic acid-dye conjugate is bound to the sugar residue of the glycated haemoglobin in this process. Non-bound dye is subsequently removed with the aid of a wash solution and the filtration medium is measured at wavelengths of 470 nm (for the total amount of haemoglobin) and 630 nm (for the blue dye which is bound via boronic acid to glycated haemoglobin).

A disadvantage of this method is that several steps are required for the procedure and in each of which the required liquids (sample, precipitation solution, wash solution) have to be exactly dosed.

The object of the invention is to eliminate the disadvantages of the prior art. In particular the object of the present invention is to provide a simple and rapid method and a corresponding analytical test element for the determination of the ratio of glycated to non-glycated haemoglobin in a sample.

The object is achieved by the subject matter of the invention as defined in the patent claims.

SUMMARY OF THE INVENTION

The invention concerns a method for the determination of the ratio of glycated to non-glycated haemoglobin in the sample, wherein
(i) the sample is optionally haemolysed in order to release cell-bound haemoglobin,
(ii) the sample is contacted with an excess of signal-generating molecules during which a fraction of the signal-generating molecules binds to glycated haemoglobin in the sample,
(iii) the fraction of signal-generating molecules that is not bound to glycated haemoglobin is separated from the sample,
(iv) the signal-generating molecules are determined in the sample which contains signal-generating molecules bound to glycated haemoglobin as well as non-glycated haemoglobin, as a measure for the glycated haemoglobin and the total amount of haemoglobin is determined, and
(v) the ratio of glycated to non-glycated haemoglobin in the sample is determined from the values obtained according to step (iv).

The method according to the invention is suitable for the determination of the relative proportion of glycated haemoglobin in relation to the total amount of haemoglobin in a blood sample. Glycated haemoglobin (GHb) which is also occasionally referred to as glycosylated or glycosidated haemoglobin is to be understood as that haemoglobin fraction which contains the main fractions haemoglobin A1a (HbA1a), haemoglobin A1b (HbA1b) and haemoglobin A1c (HbA1c).

The method according to the invention is particularly suitable for blood as the sample material. In this connection fresh capillary blood as well as blood treated with anticoagulants or dried and redissolved blood such as that which occurs for example when using so-called "sample letters" can be used. Haemolysed blood (haemolysate) or haemoglobin isolated from blood which optionally must be dissolved again for analysis by the method according to the invention, are suitable as sample materials.

Cell-bound haemoglobin, for example from erythrocytes, is released by haemolysis of the blood sample and is thus only then made accessible for the determination according to the invention. The blood sample can be haemolysed by well-known methods such as e.g. by adding haemolysis reagents such as saponin, sodium dodecyl sulfate (SDS) and/or quarternary ammonium salts, addition of saponin being preferred.

It is important for the method according to the invention that the glycated haemoglobin in the sample is contacted with signal-generating molecules which selectively bind to the glycated haemoglobin and thus label it and make it detectable. Suitable signal-generating molecules are in particular direct labels, enzyme labels or radiolabels which can bind selectively to glycated haemoglobin but not to non-glycated haemoglobin via a boronic acid group or another specific binding partner such as an antibody.

The signal-generating molecules are preferably a conjugate composed of one or several dihydroxyboryl residues or salts thereof which are bound to a signal-generating label. These boronic acid conjugate compounds or salts thereof particularly preferably have an absorption maximum at a wavelength which is outside of the range in which haemoglobin absorbs. The absorption maximum should preferably be above 600 nm. These compounds can be described by the general formula I

$$V\text{—}W\text{—}B(OH)_2 \qquad (I)$$

in which V is a cyanine, phenoxazine, phenothiazine or triphenylmethane chromophore and/or fluorophore residue which has an absorption maximum of not less than 600 nm and W is an organic bridge group. Numerous compounds of this kind and their use in methods for the determination of glycated proteins are known to a person skilled in the art for example from U.S. Pat. No. 5,631,364, EP-A 0 557 357 and the prior art cited therein. Explicit reference is herewith made to these documents.

The sample can be contacted with the signal-generating molecules by adding the signal-generating molecules as a solid, solution, dispersion etc. to the sample. Alternatively it is also possible to add the sample to the signal-generating molecules which are for example present in a soluble form in a reaction vessel or a porous matrix. In this connection it is important that the signal-generating molecules can be dissolved in the sample. Hence they may not be indissolubly immobilized.

In order to ensure that the largest possible proportion of the glycated haemoglobin in the sample interacts with the signal-generating molecules, it is advantageous to use an excess of signal-generating molecules. A fraction of the signal-generating molecules binds to glycated haemoglobin when the method according to the invention is carried out. Preferably all glycated haemoglobin contained in the sample is bound by signal-generating molecules and is thus made detectable and distinguishable from non-glycated haemoglobin. Binding of the signal-generating molecules to the glycated haemoglobin can, as mentioned above, for example be achieved by selective affinity interaction of a molecular moiety of the signal-generating molecules with the glycated haemoglobin. This can for example take place by means of an antigen-antibody interaction or by means of the affinity of boronic acids for diol structures in the sugar residue of glycated haemoglobin which is preferred according to the invention.

It is important for the method according to the invention that the fraction of signal-generating molecules which is not bound to glycated haemoglobin when contacted with the sample, is separated from the sample. This is an important distinction between the method according to the invention and methods of the prior art. In the prior art haemoglobin, glycated haemoglobin and labelled glycated haemoglobin are separated commonly or in fractions from the sample and are determined separately or together after separating the sample. The method according to the invention does without the separation of haemoglobins from the sample. Hence it does not require the elaborate separation steps which were necessary in the previously common methods and which have led to multistep and slow methods of determination which are difficult to automate.

There are several methods that come into consideration according to the invention for separating the signal-generating molecules from the sample which are present dissolved in the sample after being brought into contact with it. For this it is preferable to utilize the fact that the signal-generating molecules have a residue which can selectively interact with glycated haemoglobin. This selective interaction can, as mentioned above, for example be due to the fact that the signal-generating molecules carry an antibody against glycated haemoglobin or have a boronic acid residue which can bond to diol structures of glycated haemoglobin. In one embodiment of the method according to the invention the separation of the signal-generating molecules from the sample can be achieved in that the portion of signal-generating molecules that are not bound to glycated haemoglobin are bound by contact with immobilized glycated haemoglobin (in the case that antibodies against this are used) or with immobilized diols (if boronic acid residues are used) and are thus removed from the sample. This can for example be achieved by passing the sample containing non-bound signal-generating molecules through a permeable material which contains the above-mentioned immobilized structures. It is, however, also possible to immobilize the aforementioned immobilized structures on magnetic particles and to remove these from the sample by applying a magnetic field after incubating the sample with the magnetic particles and binding of the signal-generating molecules to the magnetic particles. In all these variants it is advantageous that the affinity of the signal-generating molecules for glycated haemoglobin in the sample is higher than for the immobilized structures so that previously formed complexes of glycated haemoglobin from the sample and the signal-generating molecules are preserved for the subsequent detection.

According to the invention it is preferable to separate the signal-generating molecule from the sample, preferably the boronic acid-dye conjugates described above, by utilizing electrostatic interactions. In this case one utilizes the fact that at pH values which are at least one unit greater than the $pK_s$ of the boronic acid-dye conjugates, the free boronic acid-dye conjugates i.e. those that are not bound to glycated haemoglobin have a higher negative charge density in comparison to free haemoglobin and in comparison to the complex of glycated haemoglobin and the boronic acid-dye conjugate. The free boronic acid-dye conjugates can in this case for example be separated from the sample by passing the sample through a porous, permeable material which has a positive charge on the outside. Membrane materials made of nylon in particular a nylon 66 modified with quarternary ammonium groups which is for example distributed as Biodyne B from the Pall company have for example proven to be particularly suitable for this. Whereas the sample and in particular the haemoglobin and the complex of glycated haemoglobin and boronic acid-dye conjugate contained therein can flow rapidly into and through the porous, permeable material, this is not possible for the free boronic acid dye conjugates. The (total) haemoglobin and glycated haemoglobin can be determined in the permeable material or after the sample has flowed through the permeable material.

It is also possible to utilize other molecular interactions to separate haemoglobin and labelled glycated haemoglobin from the signal-generating molecules for example interactions with adsorptive materials such as e.g. silica gel and aluminium oxide.

In principle known methods can be used to determine haemoglobin and glycated haemoglobin. Measurement of absorbance, reflection or fluorescence is particularly preferred for haemoglobin. These measuring methods can be used analogously for glycated haemoglobin but in the method according to the invention it is preferable to measure in this case at wavelengths at which haemoglobin does not have any absorption, reflection or fluorescence. This is due to the fact that in the method according to the invention no separation of non-glycated haemoglobin and glycated haemoglobin takes place and thus both haemoglobins are present together and have to be detected concurrently. For the determination of glycated haemoglobin, enzyme activity (in the case of enzyme label) or radioactivity (in the case of radiolabel) may also be determined depending on the type of signal-generating molecule.

The determination of the ratio of glycated to non-glycated haemoglobin in the sample or the equivalent determination of the percentage of glycated haemoglobin relative to the total haemoglobin content of the sample is also carried out by common methods known to a person skilled in the art. The ratio is preferably determined by means of calibration curves with known Hb/GHb values and comparing the measured data with the calibration data.

A further subject matter of the invention is an analytical test element which is suitable for the determination of the ratio of glycated to non-glycated haemoglobin in a sample in particular by the new method according to the invention. The test element according to the invention contains adjacent to and/or above one another a sample application zone a reagent zone in which haemolysis reagents are present to release cell-bound haemoglobin and/or which contains non-immobilized signal-generating molecules, a separation zone for separating signal-generating molecules that are not bound to glycated haemoglobin and a detection zone, wherein the zones are located on or in one or several porous matrix materials and are in contact with one another enabling liquid transfer or can be brought into such a contact.

The individual zones of the test element according to the invention signify functional areas within the test element architecture. They can be designed as flat i.e. essentially two-dimensional, and as three-dimensional zones. It is possible according to the invention that a physical region for example a section of a porous matrix material of the test element combines several zones. For example the sample can be applied directly onto a region of the test element containing reagents. In this case the sample application zone and reagent zone are in one and the same physical region. It is also possible that the detection zone and separation zone are in a common physical region.

According to the invention the zones are located on or in several porous matrix materials and it is preferable that the test element contains at least two matrix materials. Suitable porous matrix materials are for example fleeces, papers, fabrics and knitted fabrics made of natural, synthetic organic or inorganic fibrous materials. Also suitable are membranes, sponges, wicks, foamed materials, layers containing adsorbents such as silica gel or aluminium olide and such like.

Fleeces, fabrics and membranes are preferred. The liquid transport within or into the matrix material is essentially due to hydrostatic and/or capillary forces.

The individual zones should, according to the invention, be in a contact with one another which enables liquid transfer or can be brought into such a contact. Sample liquid which is applied to the sample application zone must be able to penetrate into the reagent zone from there. From there the sample liquid must be able to reach the separation zone and after separation of the signal-generating molecules that are not bound to glycated haemoglobin, it must be possible for it to advance into the detection zone. This is preferably achieved in that the individual zones, which can at least partially have different matrix materials, are each in pairwise contact or optionally completely or partially overlap. It is also possible that the individual zones are contained on or in a single matrix material. On the other hand it is also possible that additional zones are present between the individual aforementioned zones which, however, enable liquid transfer from one zone to the next. Such zones can be generally referred to as transport zones. It is also possible that individual zones are firstly not in a liquid-transfer-enabling contact with one another but are only brought into such a contact by external action. For example the separation and detection zones can be accommodated together on a separate carrier which is connected to the carrier on which the sample application and reagent zones are attached by means of a movable connection e.g. a hinge. This carrier is then like a flap which produces a liquid transfer enabling contact between the reagent zone and separation zone when the surfaces containing the zones of the one carrier are pressed onto the second carrier. Similar constructions are in principle known and described for example in U.S. Pat. No. 5,426,030.

The individual zones can either be arranged essentially next to one another or essentially above one another. It is also possible that a part of the zones is arranged essentially above one another whereas another part of the zones is arranged essentially next to one another.

The porous matrix material or materials can either be self-supporting or be mounted on or incorporated in a supporting, non-absorbent material. The matrix materials according to the invention are preferably not self-supporting. They are therefore preferably mounted on a supporting material as an inert support. Materials that are suitable as support materials are for example plastic foils and moulded plastic parts, coated cardboards, glass, ceramics, metal sheets and such like. The support should preferably be inert towards the sample materials and reagents that are used, not be attacked by these or react with them. Foils made of inert, water-resistant plastics such as polyethylene, polypropylene, polystyrene, polycarbonate, polyethylene terephthalate and such like have for example proven to be suitable according to the invention.

When using foils or other lamellar materials as inert supports, the porous matrix materials are attached to these for example by glueing or welding. The matrix materials are preferably attached to the supports by double-sided adhesive6tapes or by hot-melt adhesive. If three-dimensional moulded plastic parts are used as a support—or in this case it is better to refer to them as a housing—it is for example also possible to clamp the matrix materials between two halves of a housing which can be closed to form a housing. These and other assembly techniques are known to a person skilled in the art.

The sample application zone of the test element according to the invention is used to apply the sample liquid. It can be designed as an individual separate area of the test element or it can be a component of the reagent zone. The sample application zone is preferably marked as such for the user for example by providing it with a mark or a colour. The sample application zone directly or indirectly borders the reagent zone and is in a contact with this that enables liquid transfer so that sample liquid can pass from the sample application zone into the reagent zone. The sample application zone is preferably one of the exposed surfaces of the reagent zone or of the porous matrix material containing the reagent zone.

The purpose of the reagent zone is to provide the reagents that are required to detect glycated haemoglobin and to enable the interaction between glycated haemoglobin and the reagents. The reagent zone preferably contains the signal-generating molecules that have already been described above in connection with the method according to the invention which can bind to glycated haemoglobin to form a detectable complex. According to the invention the signal-generating molecules are in an excess relative to the expected amount of glycated haemoglobin in the sample. In addition the reagent zone can contain buffer substances and other auxiliary substances such as haemolysis reagents like saponin, sodium dodecylsulfate (SDS) or quarternary ammonium salts. The reagents are preferably present in a dissolvable form as solids in the reagent zone. They can be present mixed together and homogeneously dispersed in the reagent zone. It is, however, also possible to provide individual compartments of the reagent zone with different reagents and to even optionally accommodate them in different porous matrix materials which can be combined in the test element to form a zone. The reagents can be incorporated in the reagent zone by common methods known to a person skilled in the art for example by impregnating the reagents from appropriate solutions. The reagent zone is preferably a porous, inert fleece material for example a glass fibre fleece or a fleece made of plastic fibres in which the reagents have been incorporated and are homogeneously dispersed by impregnation and subsequent drying.

According to the invention it is also possible to only provide part of the reagents that are necessary to detect glycated haemoglobin in the reagent zone of the test element according to the invention. For example only haemolysis reagents may be present in the reagent zone. The signal-generating molecules can then either be applied to the test element before and after application of the sample liquid or be applied together with the sample after this has been optionally mixed with the reagents. It is also possible to only provide the signal-generating molecules in the reagent zone and to apply the other reagents such as the haemolysis reagents separately or together with the sample liquid.

In a particularly preferred embodiment of the test element according to the invention the reagent zone contains a porous inert fleece material impregnated with signal-generating molecules and optionally with buffer substances and other auxiliary substances on which a fabric is mounted on the side facing the sample application side which contains haemolysis reagents. In this preferred embodiment the sample is applied to the fabric which is in contact with the fleece which enables transfer of liquid.

The reagent zone of the test element according to the invention directly or indirectly borders the separation zone. Both zones are in contact with one another enabling transfer of liquids so that sample liquid located in the reagent zone can pass into the separation zone after incubation with the reagents.

It has proven to be preferable to incubate the sample liquid with the reagents of the reagent zone as long as possible so that the formation of a complex between the signal-generating molecules and glycated haemoglobin can be as complete as possible. For this purpose it is preferred according to the invention that a retardation zone is introduced between the reagent zone and the separation zone of the test element. This must take into consideration whether the dissolution of the reagents in the reagent zone or the reaction of the dissolved reagents with the glycated haemoglobin is rate-determining. Different methods are suitable for the retardation depending on the type of rate-determination.

If the rate-determining step is mainly due to the dissolution of the reagents in the sample, the sample liquid should be kept in the reagent zone for as long as possible i.e. at least until the reagents have completely dissolved. In this case the retardation zone can be achieved by placing a material with delayed solubility or a hydrophobizing material as a coating at the contact or overlapping zone between the reagent zone and separation zone. In this case the advance of the sample liquid into the separation zone is slowed down and it is kept longer in the reagent zone compared to test elements which have no retardation zone. It is also possible to create a retardation zone between the reagent zone and separation zone by mounting a porous matrix material such as a fleece with a low cross-section compared to the cross-section of the adjoining zones as a connecting zone or transport zone between the reagent zone and separation zone. This creates a bottle-neck in the transport of sample liquid which also leads to a longer stay of the sample liquid in the reagent zone than would be the case if no such retardation zone were present.

If the rate-determining step is not the dissolution of the reagents but rather the formation of a complex between glycated haemoglobin and the signal-generating molecules, it is sufficient to provide a retardation zone comprising a long porous transport path or a reservoir for holding the sample liquid which contains dissolved reagents from the reagent zone for example in the form of a voluminous fleece with a high storage capacity for liquid, between the reagent zone and separation zone.

The purpose of the separation zone is to separate signal-generating molecules dissolved in the sample liquid from the sample liquid and in particular from haemoglobin and complexes formed in the reagent zone composed of glycated haemoglobin and signal-generating molecules. The separation zone preferably contains a porous membrane or a fleece which can be each wetted by the sample liquid.

The separation effect of the separation zone for signal-generating molecules can be based on the principles described above in connection with the method according to the invention. If the fact that the signal-generating molecules carry an antibody against glycated haemoglobin is utilized for the separation, then an immobilized antigen or hapten is preferably provided in the separation zone of the test element according to the invention which are for example covalently immobilized on fibres of a fleece.

The separation can also be due to the fact that the signal-generating molecules, preferably the boronic acid-dye conjugates described above, have a higher negative charge density at pH values which are at least one unit higher than the pKs of the boronic acid-dye conjugates, the free i.e. the boronic acid-dye conjugates that are not bound to glycated haemoglobin have a higher negative charge density compared to haemoglobin and to the complex of glycated haemoglobin and boronic acid-dye conjugate. The free boronic acid-dye conjugates can in this case for example be separated from the sample by passing the sample through a porous, permeable myterial which has a positive charge on the outside or contains positively charged groups. Membranes made of nylon in particular a nylon 66 modified with quarternary ammonium groups which is for example distributed as Biodyne B from the Pall company have for example proven to be particularly suitable for this. Whereas the sample and in particular the haemoglobin and the complex of glycated haemoglobin and boronic acid-dye conjugate contained therein can flow rapidly into and through the porous, permeable material, this is not possible for the free boronic acid-free dye conjugates due to electrostatic interactions with the porous matrix material.

In all the said cases care must be taken that the amount of agents capable of separating the signal-generating molecules (i.e. immobilized binding partners, groups or charges present on the surface) is sufficient to reliably remove -he fraction of signal-generating molecules that are not bound to glycated haemoglobin so that only those signal-generating molecules reach the detection zone that are bound to glycated haemoglobin. Care must also be taken that the complexes of glycated haemoglobin and signal-generating molecules are not destroyed by the separating reagents. Hence it is particularly preferred according to the invention to separate non-bound signal-generating molecules by using positively charged membranes. In particular the nylon membranes that have already been mentioned above have proven to be particularly suitable for this.

In this preferred embodiment of the test element according to the invention it is important for an optimal separating effect and also an optimal stability of the complex of glycated haemoglobin and signal-generating molecule (i.e. the boronic acid-dye conjugate) that well-defined conditions prevail in the sample liquid during their analysis. Particular attention must be paid to the pH value. This influences, on the one hand, the complex formation between glycated haemoglobin and boronic acid-dye conjugate and, on the other hand, determines the migration rate of the free conjugate through the membrane. It is preferable that the pH of the sample solution is ca. an order of magnitude higher than the pKs value of the boronic acid-dye conjugate. For example a pH of 8.5 value has proven to be particularly suitable with a $pK_s$ value of the boronic acid-dye conjugate of 7.5. According to the invention it has proven to be advantageous to set the pH value by buffer substances in the reagent zone. In particular cyclohexylaminopropylsulfonic acid (CAPS) has proven to be advantageous for this. A person skilled in the art of course knows that it is not possible to set any desired pH values when using biological samples without making the sample unusable or unfavourably influencing other reactions that are for example required to detect an enzyme label. Hence it may be necessary to influence the $pK_s$ value of the boronic acid-dye conjugate by suitable substitution in order not to have to work in unfavourably high or low pH ranges. Such measures are also known to a person skilled in the art.

A detection zone located downstream in the transport direction of the sample liquid directly or indirectly adjoins the separation zone. This may contain detection reagents for the signal-generating molecular residues of the signal-generating molecules such as chromophoric enzyme substrates if enzyme labels are used. The detection zone is preferably a component of the porous material which contains the separation zone but which is spatially separate from the separation zone.

The method according to the invention or the test element according to the invention has the following advantages:

It avoids the complicated separation of haemoglobins from the sample or even the separation of haemoglobins into individual fractions. Instead the signal-generating molecules are separated after complex formation with glycated haemoglobin which is technically easier to accomplish and can even be carried out in a flow method such as on test elements. Pretreatment of the sample and complicated intermediate steps are not required. Hence the method can also be carried out by untrained persons for example by diabetics with the aid of appropriate test elements. The measured results are provided rapidly and typically within a few minutes.

In a preferred embodiment the method only requires application of the sample liquid and determination of the signals for haemoglobin and glycated haemoglobin in the detection zone. Other liquids do not have to be dosed.

Even small sample volumes are sufficient to carry out the method. Preferred embodiments of the test element according to the invention only require a few microlitres of blood so that drawing samples causes little pain for the patient and can be, in any case, carried out without venipuncture.

The results of the determination of the ratio of glycated to non-glycated or to total haemoglobin are volume-independent over wide ranges when the method according to the invention is carried out with the test element according to the invention.

BRIEF DESCRIPTION OF THE DRAWINGS

The invention is elucidated in more detail by the following examples and figures.

Figure 1:
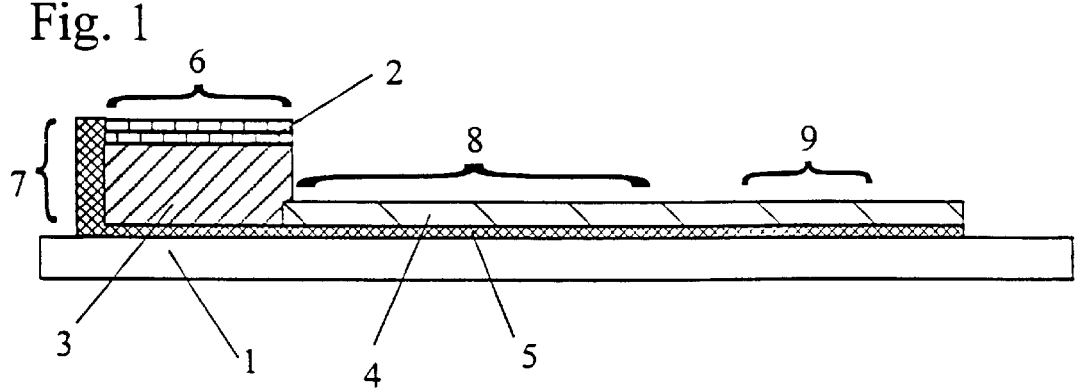
FIG. 1 and FIG. 2 each show schematically a lateral section through two preferred embodiments of the test element according to the invention in which the transport direction of the sample liquid is essentially parallel to the longitudinal axis of the test element.

The numbers in the figures denote:
1 support
2 fabric
3 first porous matrix material (fleece)
4 second porous matrix material (membrane)
5 glue
6 sample application zone
7 reagent zone
8 separation zone
9 detection zone
10 retardation zone
11 detection opening
12 sample application opening
13 housing half

DETAILED DESCRIPTION OF THE INVENTION

FIG. 1 shows a schematic longitudinal section through a preferred, strip-shaped embodiment of the test element according to the invention. A fabric (2), a first porous matrix material (fleece) (3) and a second porous matrix material (membrane) (4) are mounted on a strip-shaped support (1) with the aid of an adhesive (5), for example a hot-melt adhesive or a double-sided adhesive tape. The fabric (2) covers the first porous matrix material (3) and the first porous matrix material (3) slightly overlaps the second porous matrix material (4) to enable liquid transfer between the materials.

The surface of the fabric (2) facing away from the support (1) serves as a sample application zone (6). The fabric (2) and the first porous matrix material (3) contain the reagents which are required to selectively label the glycated haemoglobin in the sample such as buffer salts, haemolysis reagents and signal-generating molecules. Hence the fabric (2) and the first porous matrix material (3) serve as a reagent zone (7).

The section of the second porous matrix material (4) which adjoins the reagent zone (7) serves to capture free signal-generating molecules from the sample liquid which were dissolved from the reagent zone (7) by the sample liquid and could not react with glycated haemoglobin. This area is referred to as the separation zone (8). Depending on the separation principle, immobilized selective binding partners for the signal-generating molecules may be present in the separation zone (8) or the matrix material (4) itself can cause the separation for example as a result of electrostatic interactions with the free signal-generating molecules dissolved in the sample.

The detection zone (9) adjoins the separation zone (8) in the second porous matrix material (4) in which the total haemoglobin and the glycated haemoglobin labelled with signal-generating molecules are detected. This can for example be achieved either directly by measuring the reflection of haemoglobin and suitable properties of the signal-generating label (for example direct label, radio-label) bound to glycated haemoglobin or indirectly via reaction products which form as a result of the action of the signal-generating label (e.g. enzyme labels). In the latter case it may be necessary to provide detection reagents in the detection zone (9) which can generate a detectable signal in the presence of the signal-generating label. In this case the detection can be from that side of the second porous matrix material (4) which faces away from the support (1). In this case it is possible to manufacture the support (1) from a non-transparent material. However, the detection can also be carried out from the side facing the support (1). This is for example possible in a preferred embodiment in which transparent materials are used for the support (1) and adhesive (5) or in which the detection is through an opening in the support (1) and the adhesive layer (5) in the area of the detection zone (9).

The strip-shaped test element shown in a schematic longitudinal section in FIG. 2 corresponds essentially to the test element structure as described in connection with FIG. 1. In contrast to the test element of FIG. 1, a retardation zone (10) is located in this additional preferred embodiment between the reagent zone (7) and the separation zone (8) i.e. between the first porous matrix material (3) and the second porous matrix material (4). In the particularly preferred embodiment shown in FIG. 2, the retardation zone (10) is achieved by an additional porous matrix material which has a considerably smaller cross-section than that of the first porous matrix material (3) and of the second porous matrix material (4). This slows down the sample liquid transport from the reagent zone (7) into the separation zone (8) compared to the embodiment shown in FIG. 1. The result of this measure is that the sample liquid remains for a longer period in the reagent zone (7) where the longer retention time is utilized to dissolve the reagents from the reagent zone (7) and to allow complex formation between signal-generating molecules and glycated haemoglobin.

Figure 2:
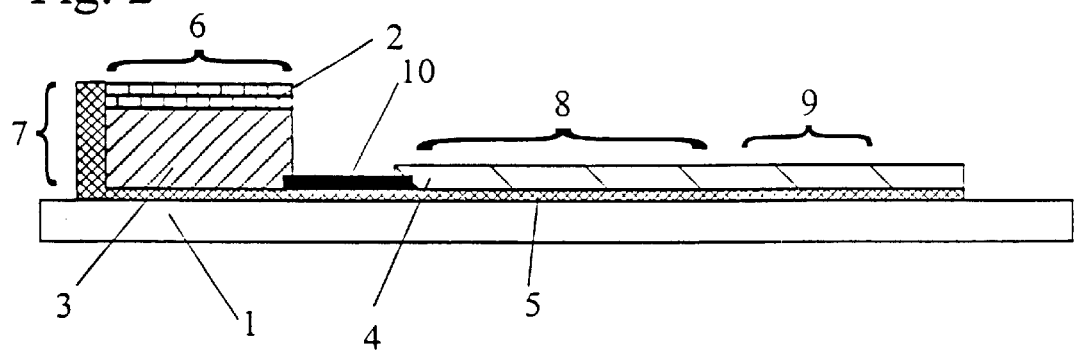
Figure 3:
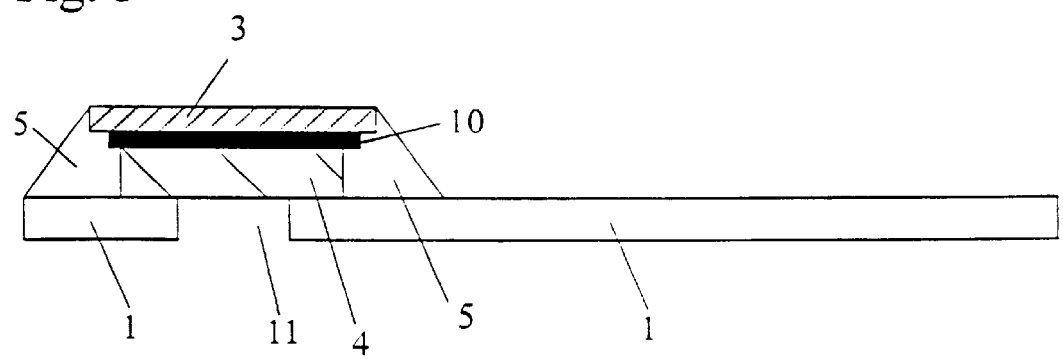
FIG. 3 shows schematically a lateral section through an additional preferred embodiment of the test element according to the invention in which the transport direction of the sample liquid is essentially perpendicular to the longitudinal axis of the test element.

Whereas the sample liquid transport in the strip-shaped test elements of FIGS. 1 and 2 takes place essentially parallel to the longitudinal axis of the test element, a further preferred embodiment of a strip-shaped test element is shown in FIG. 3 in a schematic longitudinal section in which the sample liquid transport occurs essentially perpendicular to the longitudinal axis of the test element. In the preferred test element shown here, sample liquid is applied to the upper side of the first porous matrix material (3) i.e. to the side facing away from the support (1). Haemoglobin and glycated haemoglobin are detected in this case through an opening (11) in the support (1) which for example can be designed as a circular hole or as a rectangular slit. Whereas in FIGS. 1 and 2 the individual functional zones of the test element according to the invention are arranged essentially next to one another on the support (1), these zones are mounted essentially on top of one another in a stack-like structure in the embodiment shown in FIG. 3. The second porous matrix material (4), the retardation zone (10) and the first porous matrix material (3) are attached in layers on the support (1) in this order for which hot-melt adhesive (5) is particularly suitable which holds the individual layers in contact with one another at their edges and attaches them to the support (1).

Since the separation of the signal-generating molecules that are not bound to glycated haemoglobin occurs in the second porous matrix material (4) directly over the detection opening (11) of the test element according to the invention and thus the unbound signal-generating molecules are located directly above the detection opening within the second porous matrix material (4), it is advantageous that the second porous matrix material (4) is optically non-transparent so that only sample material can be observed which reaches that surface of the second porous matrix material (4) which is exposed through the detection opening (11).

Figure 4:
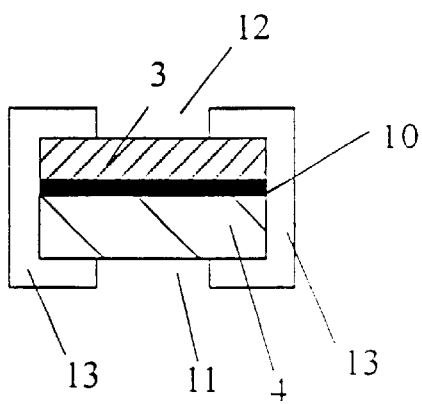
FIG. 4 shows schematically a lateral section through an additional preferred embodiment of the test element according to the invention.

In the case of a stacked arrangement of the individual zones (6 to 10) as shown in FIGS. 3 and 4, the retardation zone (10) is preferably mounted on the first (3) or second (4) porous matrix material as a layer of a slowly dissolving substance. Alternatively it can also be designed as a hydrophobizing coating on one of the two matrix materials (3, 4).

A further preferred embodiment of the test element according to the invention is shown in FIG. 4. Like FIG. 3 the first porous matrix material (3), the retardation zone (10) and the second porous matrix material (4) are layered on top of one another in a stack. Whereas this stack-like composite is arranged on a strip-like support material (1) in FIG. 3, the embodiment of FIG. 4 is characterized in that the laminar layer structure is held together by two housing half-members (13). The housing and the layers that are held together in it can have any desired cross-section such as round, quadratic or rectangular. A sample application opening (12) is provided for sample application. The detection takes place through a detection opening (11). Both openings (11, 12) can be directly opposite or staggered.

EXAMPLE 1

Manufacture of the Test Element According to the Invention of FIG. 1

A 6 mm wide and 11 mm long piece of a positively charged, 150 μm thick nylon membrane (Biodyne B, 3 μm pore size, Pall) was glued onto a 6 mm wide and 50 mm long strip of a transparent support foil made of polyester (Melinex O clear, thickness 175 μm, ICI) with the aid of a double-sided adhesive tape.

A 6 mm wide, 4.5 mm long and 720 μm thick piece of glass fibre fleece (60 g/m$^2$) was impregnated with a solution containing cyclohexylaminopropylsulfonic acid (CAPS) as a buffer substance and the boronic acid-dye conjugate XC-DAPOL-CPBA (5-[[[3-[(4-boronobenzoyl)-amino]-2-hydroxypropyl]amino]sulfonyl]-2-[[4-(ethylamino)-3-methylphenyl]-[4-(ethylimino)-3-methyl-2,5-cyclohexadien-1-ylidene]-methyl]-benzenesulfonic acid, CAS No. 191231-97-7, formula II) obtainable according to U.S. Pat. No. 5,631,364 and dried.

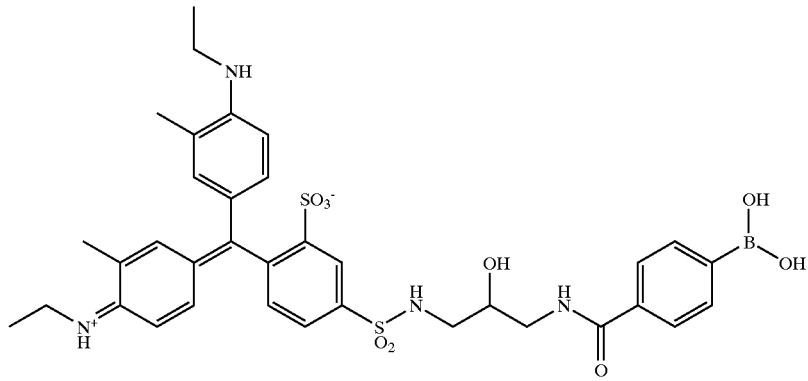

II

The dried fleece prepared in this manner contained:

| boronic acid-dye conjugate | 10 μg |
|---|---|
| CAPS | 0.44 mg |

A 6 mm wide and 5 mm long polyester fabric (280 HC, 250 μm thickness, Sefar) was impregnated with a solution containing saponin, dioctylsodium sulfonate and diamylsodium sulfonate and dried. The fabric contained:

| | |
|---|---|
| saponin | 60 µg |
| dioctylsodium sulfonate | 15 µg |
| diamylsodium sulfonate | 15 µg |

The fabric treated in this manner was mounted using a double-sided adhesive tape on the fleece that had been previously attached to the support foil with double-sided adhesive tape so that the fabric completely covered the fleece and a narrow overlap of ca. 1 mm was formed between the fleece and membrane. In the final, strip-like test element, the function of the fabric was as a sample application zone, and the fabric and glass fibre fleece served as the reagent zone. The area of the membrane adjoining the fleece served as a separation zone whereas the area of the membrane facing away from the fleece served as a detection zone.

EXAMPLE 2

Determination of the Proportion of Glycated Haemoglobin Relative to Total Haemoglobin With the Aid of the Method According to the Invention Using the Test Element from Example 1

Blood was applied as a sample material to the exposed surface of the fabric of the test element from example 1. After the sample material had reached the detection zone, the reflectance values were determined in the detection zone at wavelengths of 540 nm for the determination of total haemoglobin, at 630 nm for the determination of glycated haemoglobin and at 700 nm for the determination of the transparency of the test element. The concentration of total haemoglobin and glycated haemoglobin were calculated according to the Kubelka-Munk equation and after division, multiplied with a conversion factor in order to obtain the relative proportion of HbA1c.

Figure 5:
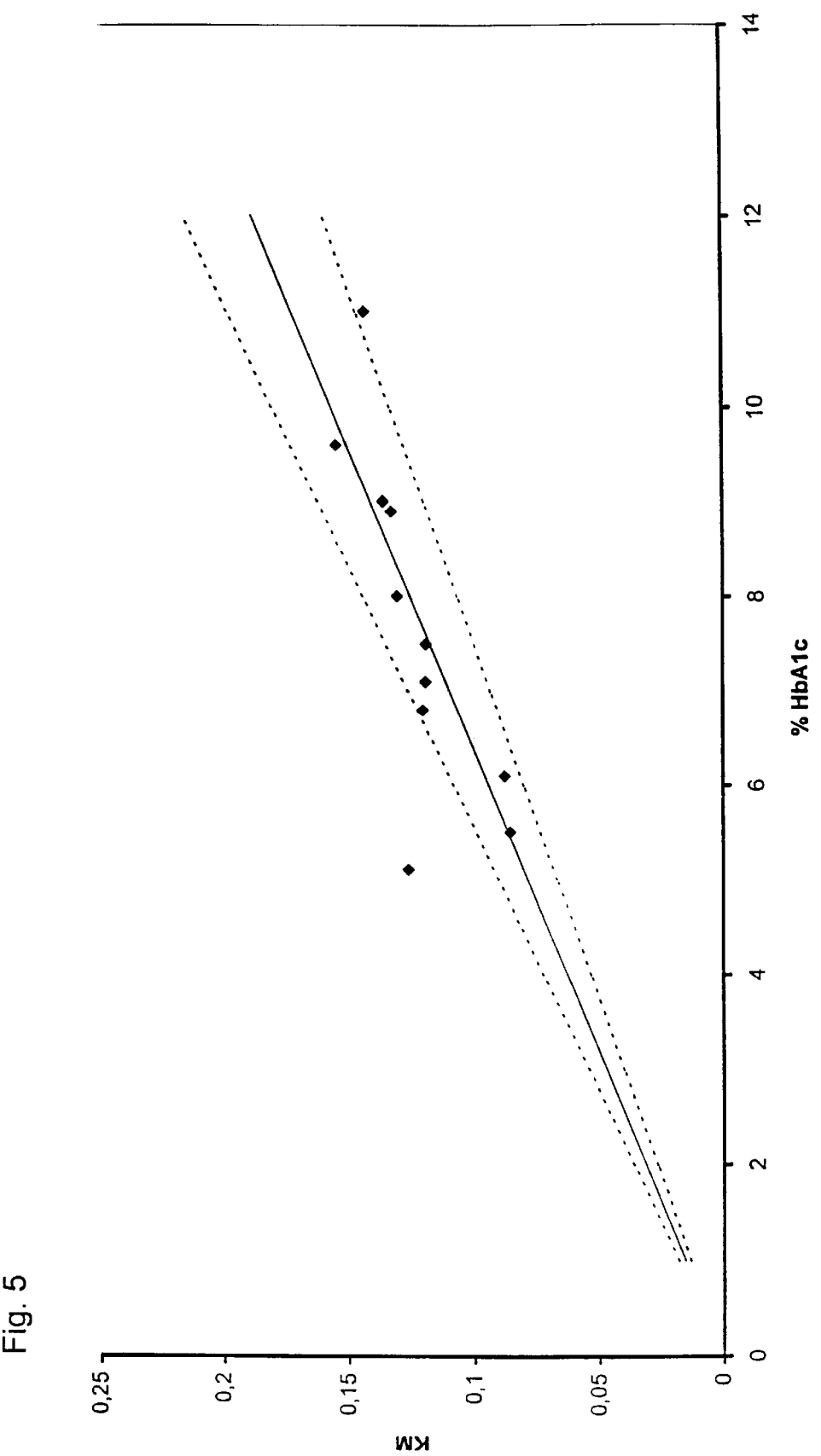
FIG. 5 shows a calibration line for diabetic blood obtained by linear regression in which the Kubelka-Munk-quotient (KM, y-axis) was plotted versus the relative amount of HbA1c relative to total haemoglobin (% HbA1c, x-axis).

The results of a measurement series with various blood samples from diabetics is shown in FIG. 5.

What is claimed is:

1. An analytical test element for determining the ratio of glycated to non-glycated haemoglobin in a sample, the test element comprising:

a sample application zone;

a reagent zone in which non-immobilized signal-generating molecules are present in excess relative to an expected amount of glycated haemoglobin in the sample or which contains one or more haemolysis reagents to release cell-bound haemoglobin or both a fraction of the non-immobilized signal-generating molecules dissolve into the sample and bind to the glycated haemoglobin in the sample;

a separation zone for separating signal-generating molecules that are dissolved in the sample but not bound to glycated haemoglobin from the sample which contains signal-generating molecules bound to glycated haemoglobin and non-glycated haemoglobin; and a detection zone for detecting the amount of non-glycated haemoglobin and for detecting the amount of signal-generating molecules bound to glycated haemoglobin, wherein one or more of the zones are located on or in at least one porous matrix material and are in contact with one another enabling liquid transfer or can be brought into such contact enabling liquid transfer from one another.

2. The analytical test element of claim 1 wherein the separation zone is a porous matrix material comprising positively charged groups.

3. The analytical test element of claim 1 wherein a retardation zone is located between the reagent zone and the separation zone.

4. The analytical test element of claim 1 wherein the at least one porous matrix material is mounted on an inert support.

5. The analytical test element of claim 1 wherein the sample comprises non-immoblized signal generating molecules prior to introduction in the sample application zone.

6. An analytical test element comprising:

a sample application zone for receiving a sample comprising haemoglobin and glycated haemoglobin;

a reagent zone for contacting the sample with a reagent comprising non-immobilized signal-generating molecules or haemolysis reagents or both, said non-immobilized signal generating molecules provided in an excess amount sufficient to convert substantially all of the glycated haemoglobin in the sample to a detectable complex comprising signal generating molecules bound to glycated haemoglobin;

a separation zone comprising a porous matrix material including positively charged groups provided to retain any non-immoblized signal generating molecules in the sample; and a detection zone for detecting the amount of detectable complex or a total amount of haemoglobin or both in the sample, wherein one or more of the zones are located on or in at least one porous matrix material and are in contact with one another or can be brought into contact with one another to allow liquid transfer through the zones.

7. The analytical test element of claim 6 wherein the detection zone is adapted to detect a total amount of glycated haemoglobin, non-glycated haemoglobin and detectable complex in the sample.

8. The analytical test element of claim 6 wherein the sample comprises non-immoblized signal generating molecules prior to introduction in the sample application zone.

9. The analytical test element of claim 6 wherein the porous matrix material comprises a nylon membrane.

10. The analytical test element of claim 9 wherein the nylon membrane contains quarternary ammonium groups.

11. The analytical test element of claim 6 wherein a retardation zone is located between the reagent zone and the separation zone.

12. The analytical test element of claim 6 comprising at least one porous matrix material mounted on an inert support.

13. The analytical test element of claim 6 wherein the reagent zone comprises at least one buffer substance.

14. The analytical test element of claim 6 wherein the signal generating molecules comprise a conjugate of one or several dihydroxyboryl residues or salts thereof, which are bound to a signal-generating label.

15. The analytical test element of claim 6 wherein the signal generating molecules comprise boronic acid conjugate compounds with an absorption maximum of not less than 600 nm or salt thereof wherein the compounds have the general Formula I

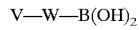

in which V is a cyanine, phenoxazine, phenothiazine or triphenylmethane chromophore or fluorophore residue which has an absorption maximum of not less than 600 nm and W is an organic bridge group.

* * * * *